United States Patent
Bachmann et al.

(10) Patent No.: US 6,800,775 B1
(45) Date of Patent: Oct. 5, 2004

(54) METAL COMPLEXES OF TRIPODAL LIGANDS

(75) Inventors: Frank Bachmann, Freiburg (DE); Josef Dannacher, Basel (CH); Menno Hazenkamp, Riehen (CH); Gunther Schlingloff, Riehen (CH); Grit Richter, Neuenburg (DE); Helena Dbaly, Muttenz (CH); Rainer Hans Traber, Reinach (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 46 days.

(21) Appl. No.: 10/031,999

(22) PCT Filed: Jul. 6, 2000

(86) PCT No.: PCT/EP00/06420

§ 371 (c)(1),
(2), (4) Date: Jan. 10, 2002

(87) PCT Pub. No.: WO01/05925

PCT Pub. Date: Jan. 25, 2001

(30) Foreign Application Priority Data

Jul. 14, 1999 (EP) ............................................ 99810631

(51) Int. Cl.$^7$ .......................... C07F 15/02; C07F 13/00; C11D 9/00
(52) U.S. Cl. ......................... 556/34; 510/174; 510/194; 510/220; 564/274; 564/275
(58) Field of Search ........................... 556/34; 564/275, 564/274; 510/220, 194, 174

(56) References Cited

U.S. PATENT DOCUMENTS

| 5,741,920 A | 4/1998 | Eckhardt et al. ............... 556/45 |
| 6,306,808 B1 | 10/2001 | Hazenkamp et al. ........ 510/224 |

FOREIGN PATENT DOCUMENTS

| DE | 19721886 | 12/1998 |
| EP | 0717103 | 6/1996 |
| GB | 2307250 | 5/1997 |
| JP | 11-50096 | * 2/1999 |
| WO | 98/54282 | 12/1998 |

OTHER PUBLICATIONS

Cook et al., Journal of Chemical Society, Dalton Transactions: Inorganic Chemistry (1976), vol. 14, pp. 1369–1375.*
Chemical Abstract 130:198180c (1999) for JP 1150096.
S. Chandra et al., J. Chem. Soc. Dalton Trans. (1993), pp. 863–869.
P. Caravan et al., J. Am. Chem. Soc. (1995), vol. 117, pp. 11230–11238.
S. Liu et al., J. Am. Chem. Soc. (1992), vol. 114, pp. 6081–6087.
K. Ramesh et al., J. Chem. Soc. Dalton Trans. (1991), pp. 3259–3262.
A. Malek et al., Synth. React. Inorg. Met.–Org. Chem., 9(2), pp. 145–155 (1979).

* cited by examiner

*Primary Examiner*—Porfirio Nazario-Gonzalez
(74) *Attorney, Agent, or Firm*—Kevin T. Mansfield

(57) ABSTRACT

Novel metal complexes of tripoadal ligands are useful as catalysts to enhance the action of peroxygen compounds in washing, cleaning and disinfecting processes.

21 Claims, No Drawings

METAL COMPLEXES OF TRIPODAL LIGANDS

The present invention relates to the use of metal complexes of tripodal ligands based on tris(2-aminoethyl)amine as catalysts which enhance the action of peroxygen compounds in washing, cleaning and disinfecting processes. The invention further relates to compositions of the metal complexes and peroxygen compounds used in such processes and to the novel metal complexes and ligands and also to processes for preparing them.

It is known that some manganese complexes, especially those of the salene type, are useful catalysts for oxidations with peroxygen compounds, especially as part of a washing processes. It is also known that certain other manganese complexes have a marked bleaching effect on dirt and dyes in wash liquors. There is nevertheless a demand for further compounds having an improved effect and/or having a broader application range, subject to the proviso that no significant fibre and dye damage may occur when applied to textile material.

It has now been found that certain metal complexes of tripodal ligands obtainable by reacting tris(2-aminoethyl)amine with aldehydes or ketones substantially meet the stated requirements when used as catalysts in that they enhance the action of peroxygen compounds in a wide variety of applications to a higher degree without occurrence of fibre and dye damage. Surprisingly, the enhanced effect occurs in applications including the following on using the metal complexes of such ligands in aqueous solution together with peroxygen compounds:

a) bleaching spots or stains on textile material as part of a washing process,
b) preventing the redepositon of migrating dyes during the washing of textile material,
c) cleaning hard surfaces, especially crockery or glass,
d) cleaning hard surfaces, especially tiles, particularly to remove mold stains,
e) using washing and cleaning solutions having an antibacterial effect, and
f) removing printing inks from printed wastepaper (de-inking).

The invention accordingly provides for the use of metal complexes containing a tripodal ligand of the formula

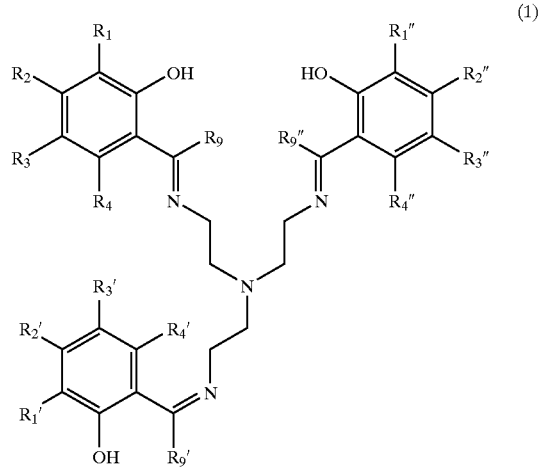

(1)

where
$R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano, halogen, $SO_3M$, where M is hydrogen, an alkali metal cation, an alkaline earth metal cation, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $R_6NR_7$, $N\oplus R_6R_7R_{10}$ or linear or branched $C_1$–$C_8$alkyl-$R_8$, where $R_8$ is $OR_5$, $COOR_5$, $NH_2$, $NHR_6$, $NR_6R_7$ or $N\oplus R_6R_7R_{10}$, where $R_6$, $R_7$ and $R_{10}$ are identical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl, as catalysts for oxidations with peroxygen compounds.

Particular preference is given to the use of Mn(III) and Fe(III) complexes containing a ligand of the above formula (1), especially an Mn(III) and Fe(III) complex which contains a ligand of the above formula (1) and metal in a molar ratio of 1:1.

Halogen is preferably chlorine, bromine or fluorine, particularly preferably chlorine.

Alkyl is particularly alkyl having 1 to 4 carbon atoms, especially methyl, ethyl, n-propyl, isopropyl, n-butyl, sec-butyl, isobutyl or tert-butyl.

$R_6$ and $R_7$ combining with the joining nitrogen atom to form a 5-, 6- or 7-ring are in particular a pyrrolidine, piperidine, morpholine or piperazine ring. The piperazine ring may be substituted, for example by alkyl, on the nitrogen atom not attached to the phenyl or alkyl radical.

Aryl is for example naphthyl or particularly phenyl.

$R_9$, $R_9'$ and $R_9''$ are each preferably independently hydrogen or $C_1$–$C_4$alkyl, especially hydrogen.

An alkali cation M in the $SO_3M$ radicals may be for example lithium, potassium or particularly sodium, an alkaline earth metal cation M is selected in particular from magnesium and calcium.

Very particular preference is given to the use of the 1:1 Me(III) complexes of the formula

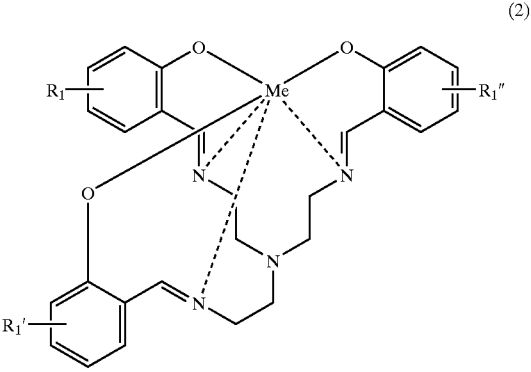

(2)

where Me is Mn or Fe, $R_1$, $R_1'$ and $R_1''$ are each independently hydrogen, $C_1$–$C_4$alkyl, $C_1$–$C_4$alkoxy, hydroxyl, nitro, $NHR_6$, $NR_6R_7$ or -$N\oplus R_5R_6R_7$, where $R_5$, $R_6$ and $R_7$ are each independently $C_1$–$C_4$alkyl, as catalysts for oxidations with peroxygen compounds.

Me in the formula (2) is preferably manganese.

The metal complexes containing a tripodal ligand of the formula (1) are preferably used in aqueous solution together with peroxygen compounds for bleaching spots or stains on textile material or for preventing the redeposition of migrating dyes as part of a washing process, or for cleaning hard surfaces, especially crockery or glass.

The ligands of the formula (1) are also useful in the uncomplexed form, as catalysts in aqueous solution with peroxygen compounds for bleaching spots or stains on textile material.

Preference for this use is given to the ligands of the formula

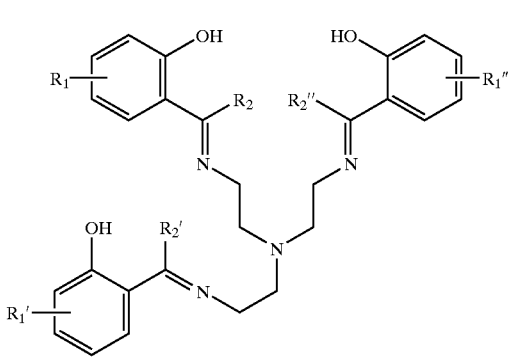

(3)

where
$R_1$, $R_1'$ and $R_1''$ are each independently hydrogen, $C_1$–$C_4$alkyl, $C_1$–$C_4$alkoxy, hydroxyl, nitro, $NHR_6$, $NR_6R_7$ or $N{\oplus}R_5R_6R_7$, where $R_5$, $R_6$ and $R_7$ are each independently $C_1$–$C_4$alkyl and $R_2$, $R_2'$ and $R_2''$ are each independently hydrogen, linear or branched $C_1$–$C_8$alkyl or aryl.

Individual metal complexes containing a tripodal ligand of the formula (1) are already known, for example from S. Chandra, P. Chakraborty, A. Charkaravorty, J. Chem. Soc., Dalton Trans. (1993), 6,863. Novel metal complexes are the manganese(III) and iron(III) complexes containing a tripodal ligand of the formula

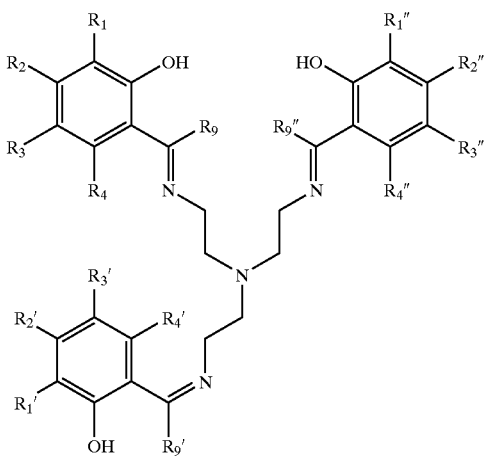

(1)

where $R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano, halogen, $SO_3M$, where M is hydrogen, sodium, calcium, magnesium, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $NR_6R_7$, $NR{\oplus}R_6R_7R_{10}$ or linear or branched $C_1$–$C_8$alkyl-$R_8$, where $R_8$ is $OR_5$, $COOR_5$, $NH_2$, $NHR_6$, $NR_6R_7$ or $N{\oplus}R_6R_7R_{10}$, where $R_6$, $R_7$ and $R_{10}$ are identical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl, subject to the condition that in the manganese(III) complex at least one of the substituents $R_1$, $R_2$, $R_3$, $R_4$, $R_1'$, $R_2'$, $R_3'$, $R_4'$, $R_1''$, $R_2''$, $R_3''$, $R_4''$, $R_9$, $R_9'$ and $R_9''$ has a meaning other than hydrogen and that at least one of the substituents $R_3$, $R_3'$ and $R_3''$ has a meaning other than chlorine when the substituents $R_1$, $R_2$, $R_4$, $R_1'$, $R_2'$, $R_4'$, $R_1''$, $R_2''$, $R_4''$, $R_9$, $R_9'$ and $R_9''$ are all hydrogen.

These manganese(III) and iron(III) complexes also form part of the subject-matter of the present invention. They are obtained in a conventional manner by reacting a ligand of the formula (1) with a manganese or iron compound to form the corresponding metal complex. Such methods of operation are described for example in U.S. Pat. No. 5,281,578 and No. 4,066,459. Also new are the ligands of the formula

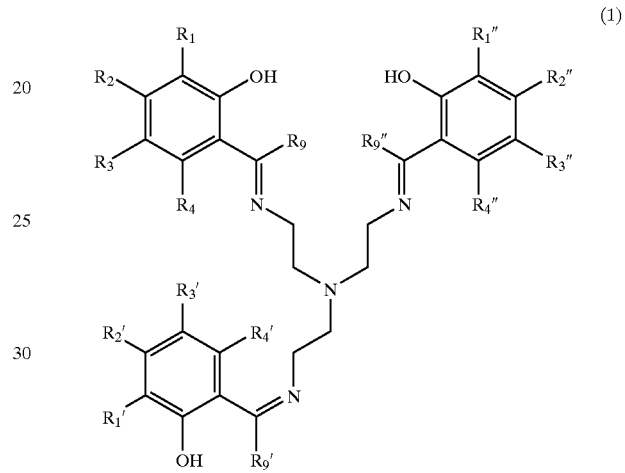

(1)

where
$R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano, halogen, $SO_3M$, where M is hydrogen, an alkali metal cation, an alkaline earth metal cation, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $NR_6R_7$, $N{\oplus}R_6R_7R_{10}$ or linear or branched $C_1$–$C_8$alkyl-$R_8$, where $R_8$ is $OR_5$, $COOR_5$, $NH_2$, $NHR_6$, $NR_6R_7$ or $N{\oplus}R_6R_7R_{10}$, where $R_6$, $R_7$ and $R_{10}$ are identical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl, subject to the condition that at least one of the substituents $R_1$, $R_2$, $R_3$, $R_4$, $R_1'$, $R_2'$, $R_3'$, $R_4'$, $R_1''$, $R_2''$, $R_3''$, $R_4''$, $R_9$, $R_9'$ and $R_9''$ has a meaning other than hydrogen and that at least one of the substituents $R_3$, $R_3'$ and $R_3''$ has a meaning other than chlorine when the substituents $R_1$, $R_2$, $R_4$, $R_1'$, $R_2'$, $R_4'$, $R_1''$, $R_2''$, $R_4''$, $R_9$, $R_9'$ and $R_9''$ are all hydrogen.

These ligands likewise form part of the subject-matter of the present invention. They are obtained in a conventional manner, for example by reacting tris(2-aminoethyl)amine with 3 mol of the substituted or unsubstituted salicylaldehyde. Reacting stepwise with three different salicylaldehydes or with mixtures of two or three different salicylaldehydes provides ligands of the formula (1) where the three aromatic rings have different substituents.

The metal complexes containing a tripodal ligand of formula (1) may before their use be converted into a solid or liquid preparation comprising the metal complex containing a tripodal ligand of the formula (1), a dispersant and optionally further ingredients and water.

It is advisable to grind the metal complexes, preferably to an average particle size of less than 20 μm, especially between 0.1 and 15 μm. Grinding may be effected together with the dispersants and further ingredients in dry form, but wet grinding is preferred. Grinding is effected in a conventional manner and in customary mills. The dry preparations obtained may be used in this form or may be slurried up in a solvent or water and used in the form of a suspension. Suspensions obtained from wet grinding may be used as such or may be dried and used in the form of solid preparations.

The present invention accordingly further provides aqueous suspensions comprising
a) 1–60% by weight, preferably 5–30% by weight, of a metal complex containing a tripodal ligand of the formula (1),
b) 0.5 to 15% by weight, preferably 1–5% by weight, of a dispersant,
c) 0–10% by weight of a further ingredient, and
d) 15–98.5% by weight of water.

The present invention further provides solid preparations comprising
a) 1–99% by weight, preferably 5–50% by weight, of a metal complex containing a tripodal ligand of the formula (1),
b) 1 to 99% by weight, preferably 50–95% by weight, of a carrier material,
c) 0–20% by weight of a dispersant,
d) 0–10% by weight of a further ingredient, and
e) 0–5% by weight of water.

Useful dispersants include in particular anionic dispersants and nonionic dispersants.

The anionic dispersants used include for example commercially available water-soluble anionic dispersants for dyes, pigments. etc. Useful products include in particular condensation products of aromatic sulfonic acid and formaldehyde, condensation products of aromatic sulfonic acids with possibly chlorinated biphenyls or diphenyl oxides and optionally formaldehyde, (mono/di-)alkylnaphthalenesulfonates, sodium salts of polymerized organic sulfonic adds, sodium salts of polymerized alkylnaphthalenesulfonic acid, sodium salts of polymerized alkylbenzenesulfonic acid, alkylarylsulfonates, sodium salts of alkylpolyglycol ether sulfates, polyalkylated polynuclear arylsulfonates, methylene-linked condensation products of arylsulfonic acids and hydroxyarylsulfonic acids, sodium salts of dialkylsulfosuccinic acid, sodium salts of alkyldiglycol ether sulfates, sodium salts of polynaphthalenemethanesulfonates, lignin- or oxyligninsulfonates or heterocyclic polysulfonic acids.

Particularly useful anionic dispersants are condensation products of naphthalenesulfonic acids with formaldehyde, sodium salts of polymerized organic sulfonic acids, (mono/di-)alkylnaphthalenesulfonates, polyalkylated polynuclear arylsulfonates, sodium salts of polymerized alkylbenzenesulfonic acid, ligninsulfonates, oxyligninsulfonates and condensation products of napthalenesulfonic acid with the polychloromethylbiphenyl.

Useful nonionic dispersants include in particular water-emulsifiable, -dispersible or -soluble compounds having a melting point of at least 35° C. The following compounds are concerned, for example:

1. fatty alcohols having 8 to 22 carbon atoms, especially cetyl alcohol,
2. addition products of preferably 2 to 80 mol of alkylene oxide, especially ethylene oxide, in which case individual ethylene oxide units may be replaced by substituted epoxides, such as styrene oxide and/or propylene oxide, with higher saturated or unsaturated monoalcohols, fatty acids, fatty amines or fatty amides of 8 to 22 carbon atoms or with benzyl alcohols, phenylphenols, benzylphenols or alkylphenols whose alkyl radicals have at least 4 carbon atoms,
3. alkylene oxide, especially propylene oxide condensation products (block polymers),
4. ethylene oxide-propylene oxide adducts with diamines, especially ethylenediamine,
5. reaction products of fatty acid of 8 to 22 carbon atoms and a primary or secondary amine having at least one hydroxyloweralkyl or loweralkylloweralkyl group, or alkylene oxide addition products of these hydroxyalkyl-containing reaction products,
6. sorbitan esters, preferably having longchain ester groups, or ethoxylated sorbitan esters, for example polyoxyethylene sorbitan monolaurate having 4 to 10 ethylene oxide units or polyoxyethylene sorbitan trioleate having 4 to 20 ethylene oxide units,
7. addition products of propylene oxide with a tri- to hexahydric aliphatic alcohol of 3 to 6 carbon atoms, for example glycerol or pentaerythritol, and
8. fatty alcohol polyglycol mixed ethers, especially addition products of 3 to 30 mol of ethylene oxide and 3 to 30 mol of propylene oxide with aliphatic monoalcohols of 8 to 22 carbon atoms.

Particularly useful nonionic dispersants are surfactants of the formula $$R_{11}\text{—O—}(\text{Alkylen—O})_n\text{—}R_{12} \quad (4)$$

where
$R_{11}$ is $C_8$–$C_{22}$alkyl or $C_8$–$C_{18}$alkenyl;
$R_{12}$ is hydrogen, $C_1$–$C_4$alkyl; a cycloaliphatic radical having at least 6 carbon atoms or benzyl;
"Alkylen" is an alkylene radical of 2 to 4 carbon atoms, and n is from 1 to 60.

The substituents $R_{11}$ and $R_{12}$ in the formula (4) are advantageously the hydrocarbon radical of an unsaturated or preferably saturated aliphatic monoalcohol of 8 to 22 carbon atoms. The hydrocarbon radical may be straight-chain or branched. Preferably $R_{11}$ and $R_{12}$ are each independently an alkyl radical of 9 to 14 carbon atoms.

Useful aliphatic saturated monoalcohols include natural alcohols, for example lauryl alcohol, myristyl alcohol, cetyl alcohol or stearyl alcohol, and also synthetic alcohols, for example 2-ethylhexanol, 1,1,3,3-tetramethylbutanol, octan-2-ol, isononyl alcohol, trimethylhexanol, trimethyinonyl alcohol, decanol, $C_9$–$C_{11}$ oxo alcohol, tridecyl alcohol, isotridecyl alcohol or linear primary alcohols (Alfols™) having 8 to 22 carbon atoms. Some representatives of these Alfols are Alfol (8–10), Alfol (9–11), Alfol (10–14), Alfol (12–13) or Alfol (16–18).

Examples of unsaturated aliphatic monoalcohols are dodecenyl alcohol, hexadecenyl alcohol and oleyl alcohol.

The alcohol radicals may be present individually or in the form of mixtures of two or more components, for example as mixtures of alkyl and/or alkenyl groups derived from soybean fatty acids, palm kernel fatty acids or tallow oils.

(Alkylen-O) chains are preferably divalent radicals of the formulae

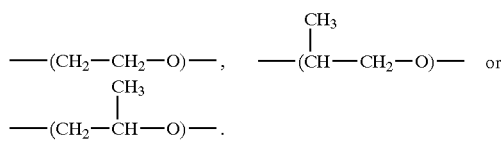

Examples of a cycloaliphatic radical are cycloheptyl, cyclooctyl or preferably cyclohexyl.

Preferred nonionic dispersants are surfactants of the formula

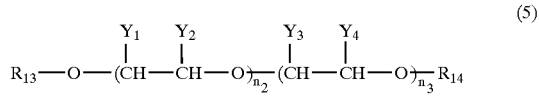

where
$R_{13}$ is $C_8$–$C_{22}$alkyl;
$R_{14}$ is hydrogen or $C_1$–$C_4$alkyl;
$Y_1$, $Y_2$, $Y_3$ and $Y_4$, are independently hydrogen, methyl or ethyl;
$n_2$ is from 0 to 8; and
$n_3$ is from 2 to 40.

Further important nonionic dispersants conform to the formula

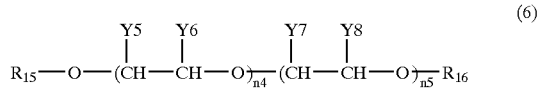

where
$R_{15}$ is $C_9$–$C_{14}$alkyl;
$R_{16}$ is $C_1$–$C_4$alkyl;
$Y_5$, $Y_6$, $Y_7$ and $Y_8$, are independently hydrogen, methyl or ethyl, subject to the proviso that
one of $Y_5$, $Y_6$ on the one hand or $Y_7$ and $Y_8$ on the other is always hydrogen; and
$n_4$ and $n_5$, are independently an integer from 4 to 8.

The nonionic dispersants of the formulae (4) to (6) may be used as mixtures. Useful surfactant mixtures accordingly include for example non-end-group-capped fatty alcohol ethoxylates of the formula (4), ie. compounds of the formula (4) where
$R_{11}$ is $C_8$–$C_{22}$alkyl.
$R_{12}$ is hydrogen and
the Alkylen-O chain is the radical —($CH_2$—$CH_2$—O)—,
and also end-group-capped fatty alcohol ethoxylates of the formula (6).

Examples of the nonionic dispersants of the formulae (4), (5) or (6) are reaction products of a $C_{10}$–$C_{13}$ fatty alcohol, for example of a $C_{13}$ oxo alcohol, with 3 to 10 mol of ethylene oxide, propylene oxide and/or butylene oxide, or the reaction product of one mole of a $C_{13}$ fatty alcohol with 6 mol of ethylene oxide and 1 mol of butylene oxide. The addition products may each be end-group-capped by $C_1$–$C_4$alkyl, preferably methyl or butyl.

These dispersants may be used individually or as mixtures of two or more dispersants.

Useful carrier materials Include for example: solid Inorganic compounds possessing little if any hygroscopicity that are compatible with laundry detergent ingredients and are soluble or readily suspendible in water. Examples are oxides, such as MgO, CaO, $TiO_2$, ZnO, $Al_2O_3$ and $SiO_2$, especially $Al_2O_3$ and $SiO_2$; borates, aluminates, silicates, carbonates, phosphates, sulfates and aluminosilicates (zeolites) of alkai and alkaline earth metals, especially of sodium and of potassium. The oxo anions in these compounds may be linked via oxygen atoms to form larger chains, rings, layers or three-dimensional networks.

Examples of further ingredients include wetting agents, water-insoluble or water-soluble dyes or pigments and also fillers and optical brighteners. These ingredients are present in an amount of 0 to 10% by weight based on the total weight of the solid or liquid preparation.

The metal complexes containing a tripodal ligand of the formula (1) are used as catalysts for oxidations with peroxygen compounds, for example for bleaching textile material, without causing significant damage to fibres and dyeings.

The present invention accordingly further provides a washing or cleaning process, which comprises adding to the liquor, which contains a peroxidic detergent, 0.1 to 200 µmol per liter of wash liquor of one or more metal complexes containing a tripodal ligand of the formula (1).

The present invention further provides a process for preventing the redeposition of migrating dyes in a wash liquor, which comprises adding to the wash liquor, which contains a peroxidic detergent, 0.5 to 150, preferably 1.5 to 75, especially 7.5 to 40, mg per liter of wash liquor of one or more metal complexes containing a tripodal ligand of the formula (1).

The present invention also provides a laundry detergent comprising
I) 5–90%, preferably 5–70%, of A) an anionic surfactant and/or B) a nonionic surfactant,
II) 5–70%, preferably 5–50%, especially 5–40%, of C) a builder,
III) 0.1–30%, preferably 1–12%, of D) a peroxide, and
IV) 0.005–2%, preferably 0.02–1%, especially 0.1–0.5% of E) a metal complex containing a tripodal ligand of the above-defined formula (1), the percentages all being percent by weight based on the total weight of the laundry detergent The laundry detergent may be in solid or liquid form, for example in the form of a liquid nonaqueous composition including not more than 5%, preferably from 0 to 1%, by weight of water, and be based on a suspension of a builder in a nonionic surfactant, as described for example in GB-A-2,158,454.

Preferably, however, the laundry detergent is powdered or granular.

A powdered laundry detergent may be produced for example by first producing a starting powder by spray drying an aqueous slurry containing all above-recited components except components D) and E) and then adding the dry components D) and E) and mixing everything together.

It is also possible to add component E) to an aqueous slurry containing components A), B) and C), then to spray dry and subsequently to mix component D) with the dry material.

It is also possible to start with an aqueous slurry which contains component A) and C), but component B) either not at all or only in part. The slurry is spray dried, then component E) is mixed with component B) and added, and subsequently component D) is mixed in dry.

The anionic surfactant A) can be for example a sulfate, sulfonate or carboxylate surfactant or a mixture thereof.

Preferred sulfates are sulfates having 12–22 carbon atoms in the alkyl radical, optionally in combination with alkyl ethoxy sulfates whose alkyl radical possesses 10–20 carbon atoms.

Examples of preferred sulfonates are alkylbenzenesulfonates having 9–15 carbon atoms in the alkyl radical.

The cation in the anionic surfactants is preferably an alkali metal cation, especially sodium.

Preferred carboxylates are alkali metal sarcosinates of the formula R—CO—N($R^1$)—$CH_2COOM^1$, where R is alkyl or alkenyl having 8–18 carbon atoms in the alkyl or alkenyl radical, $R^1$ is $C_1$–$C_4$alkyl and $M^1$ is an alkali metal.

The nonionic surfactant B) can be for example a condensation product of 3–8 mol of ethylene oxide with 1 mol of primary alcohol having 9–15 carbon atoms.

Builder C) may be for example alkali metal phosphate, especially tripolyphosphate, carbonate or bicarbonate, especially the sodium salt thereof, silicate, aluminosilicate, polycarboxylate, polycarboxylic acid, organic phosphonate, aminoalkylene-poly(alkylenephosphonate) or a mixture thereof.

Particularly useful silicates are sodium salts of crystalline sheet-silicates of the formula $NaHSi_tO_{2t+1} \cdot pH_2O$ or $Na_2Si_tO_{2t+1} \cdot pH_2O$, where t is between 1.9 and 4 and p is between 0 and 20.

Preferred aluminosilicates are those commercially available under the name zeolite A, B, X and HS and also mixtures comprising two or more of these components.

Preferred polycarboxylates are polyhydroxycarboxylates, especially citrates, and acrylates and also copolymers thereof with maleic anhydride.

Preferred polycarboxylic acids are nitrilotriacetic acid, ethylenediaminetetraacetic acid and also ethylenediaminedisuccinate not only in racemic form but also as the enantiomerically pure S,S-form.

Particularly useful phosphonates or aminoalkylenepoly (alkylenephosphonate)s are alkali metal salts of 1-hydroxyethane-1,1-diphosphonic acid, nitrilotris (methylenephosphonic acid), ethylenediaminetetramethylenephosphonic acid and diethylenetriaminepentamethylenephosphonic acid. Peroxide component D) may be selected for example from the literature-described and commercially available organic and inorganic peroxides which bleach textile materials at customary washing temperatures, for example at 10 to 95° C.

The organic peroxides concerned are for example mono- or polyperoxides, especially organic peracids or salts thereof, such as phthallmidoporexycaproic acid, peroxybenzoic acid, diperoxydodecanedioic acid, diperoxynonanedioic acid, diperoxydecanedioic acid, diperoxyphthalic acid or salts thereof.

Preferably, however, inorganic peroxides are used, for example persulfates, perborates, percarbonates and/or persilicates. It will be appreciated that mixtures of organic and/or inorganic peroxides may be used as well. The peroxides may be present in different crystal forms and with different water contents and they may also be used together with other organic or inorganic compounds to improve their stability in storage.

The peroxides are preferably incorporated into the laundry detergent by mixing of the components, for example by means of a screw metering system and/or a moving bed mixer.

In addition to the combination of the invention, the laundry detergents may include one or more optical brighteners, for example from the group consisting of bistriazinylamino-stilbenedisulfonic acid, bistriazolylstilbenedisulfonic acid, bisstyrylbiphenyl, bisbenzofuranylbiphenyl, a bisbenzoxalyl derivative, a bisbenzimidazolyl derivative, a coumarin derivative and a pyrazoline derivative.

The laundry detergent may further include soil suspenders, for example sodium carboxymethylcellulose, pH regulators, for example alkali or alkaline earth metal silicates, foam regulators, for example soap, salts for controlling the spray drying and the granulating properties, for example sodium sulfate, scents and also optionally antistats, fabric conditioners, enzymes, such as amylase, bleaching agents, pigments and/or shading agents. It will be appreciated that these ingredients have to be stable with regard to the bleaching agent used.

Further preferred ingredients of the laundry detergents according to the invention are polymers to inhibit textiles that are being washed from being tainted by dyes in the wash liquor that have become detached from the textiles under the conditions of the wash. These polymers are preferably polyvinylpyrrolidones or polyvinylpyridine N-oxides, optionally modified through incorporation of anionic or cationic substituents, especially such polymers having a molecular weight in the range from 5000 to 60,000, especially from 10,000 to 50,000. These polymers are preferably used In an amount of 0.05 to 5% by weight, especially 0.2 to 1.7% by weight, based on the total weight of the laundry detergent.

The laundry detergents of the invention may additionally include perborate activators, for example TAED, TAGU or SNOBS. Preference is given to TAED, which is preferably used in an amount of 0.05 to 5% by weight, especially 0.2 to 1.7% by weight, based on the total weight of the laundry detergent.

Surprisingly, metal complexes containing a tripodal ligand of the formula (1) also have a significantly improved bleach-catalysing effect on coloured stains on hard surfaces. A dishwashing composition that includes these complexes in catalytic amounts as well as a peroxygen compound with or without TAED (N,N,N',N'-tetraacetylethylenediamine) will substantially remove tea stains on porcelain at 45° C. in the dishwasher. This holds even for the use of hard water, in which the removal of tea stains is known to be more difficult to achieve than in soft water.

The present invention accordingly further provides for the use of metal complexes containing a tripodal ligand of the formula (1) as catalysts for reactions with peroxy compounds in cleaning solutions for hard surfaces, especially for crockery.

The present invention further provides a hard surface cleaner, especially a cleaner for crockery, a crockery cleaner for use in machine cleaning processes, comprising one of the metal complexes described above containing a tripodal ligand of the formula (1) as a bleach catalyst, and a process for cleaning hard surfaces, especially crockery, using such a bleach catalyst.

The inventive metal complexes containing a tripodal ligand of the formula (1) are also very useful for cleaning hard surfaces, especially tiles, particularly for removing mold stains. Such stains frequently occur especially in the joints between the tiles. These joints may be for example in cementitious and/or gypseous material or in polymer, for example silicone.

The invention accordingly further provides for the use of metal complexes containing a tripodal ligand of the formula (1) as catalysts for reactions with peroxygen compounds in cleaning solutions for tiles and inter-tile joints, and the cleaning solutions used for this purpose that Include a metal complex containing a tripodal ligand of the formula (1) and a peroxide with or without further ingredients such as, for example, surfactants.

The inventive metal complexes containing a tripodal ligand of the formula (1) also provide an excellent antibacterial effect when used together with peroxygen compounds. The use of the inventive metal complexes containing a tripodal ligand of the formula (1) for killing bacteria or for protecting against bacterial colonization accordingly constitutes a further part of the subject-matter of the present invention.

The examples hereinbelow illustrate the invention without limiting it. Parts and percentages are by weight, unless otherwise stated. The ligands are advantageously prepared under argon.

EXAMPLE 1

N,N',N"-Tris[salicylideneaminoethyl]amine

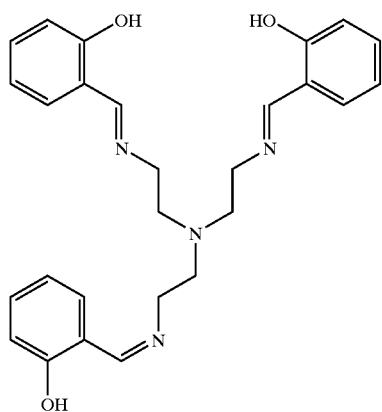

527 µl (3.42 mmol) of tris(2-aminoethyl)amine are added dropwise to a clear emulsion of 1.27 g (10.3 mmol) of salicylaldehyde in 90 ml of distilled water at room temperature to form a cloudy yellow suspension, which is subsequently stirred for 20 hours. The precipitate formed is filtered off and dried to constant weight in a vacuum drying cabinet at 35° C.

Yield 1.40 g (89%), canary-yellow solid.

$^{13}$C NMR (CDCl$_3$): δ=58.2, 60.3 (N$\underline{C}$H$_2$), 119.1, 120.8, 134.1, 134.2 (tert. aryl-C), 168.4 (C=N), 120.9, 163.4 (quart. aryl-C).

EXAMPLE 2

N,N',N"-Tris[4-N-diethylaminosalicylideneaminoethyl]amine

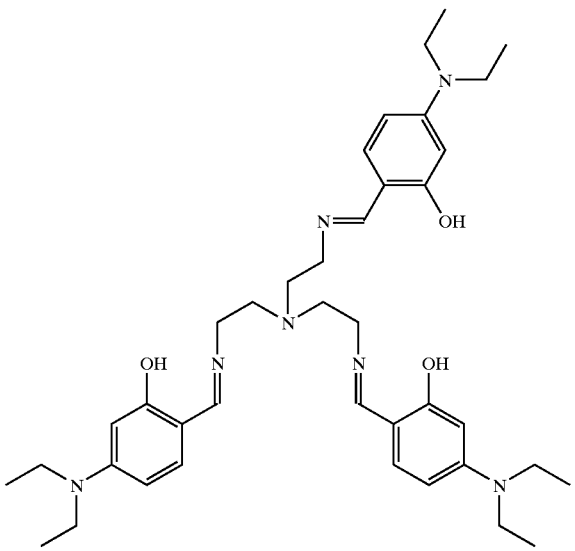

The synthesis is carried out with activated pulverized molecular sieve (3 Å) under argon. To this end, 10.0 g of molecular sieve are ground, heated with a Bunsen burner for 45 min under reduced pressure and cooled down in a stream of argon. 10 g of thusly pretreated molecular sieve and 2.03 g (10.3 mmol) of 4-(N,N-diethylamino)-2-hydroxybenzaldehyde are introduced into 90 ml of toluene at room temperature. The resulting dark red/beige suspension is admixed with 527 µl (3.42 mmol) of tris(2-aminoethyl)amine added dropwise. The reaction solution is stirred at room temperature for 25 hours. To work up, the reaction solution is filtered and the filtrate is concentrated under reduced pressure.

Yield 2.34 g (102%). beige/orange solid, still contains ethanol.

$^{13}$C NMR (CDCl$_3$): δ=12.9 (CH$_2$—$\underline{C}$H$_3$), 44.5 ($\underline{C}$H$_2$—CH$_3$), 54.5, 56.2 (N—$\underline{C}$H$_2$), 98.6, 102.6, 134.2 (tert. aryl-C), 108.3, 151.9, 169.0 (quart. aryl-C), 164.1 (C=N).

EXAMPLE 3

N,N',N''-Tris[4-N-dimethylaminosalicylideneaminoethyl]amine

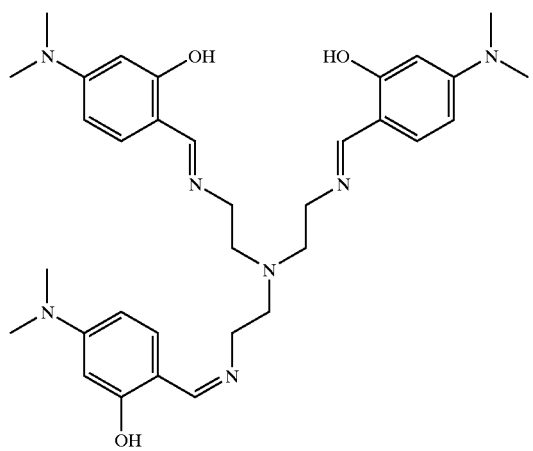

A suspension of 1.70 g (10.3 mmol) of 4-(N,N-dimethylamino)-2-hydroxybenzaldehyde, 527 µl (3.42 mmol) of tris(2-aminoethyl)amine and 10 g of activated pulverized molecular sieve (3 Å) in 90 ml of absolute toluene is prepared, reacted and worked up as described in Example 2.

Yield: 1.86 g (93%), brownish yellow solid.

$^{13}$C NMR (CDCl$_3$): δ=40.5 (N—$\underline{C}$H$_3$), 55.5, 56.7 (N—$\underline{C}$H$_2$), 99.8, 103.7, 134.0 (tert. aryl-C), 109.2, 154.6, 168.2 (quart. aryl-C), 164.7 (C=N).

EXAMPLE 4

N,N',N''-Tris[4-methoxysalicylideneaminoethyl]amine

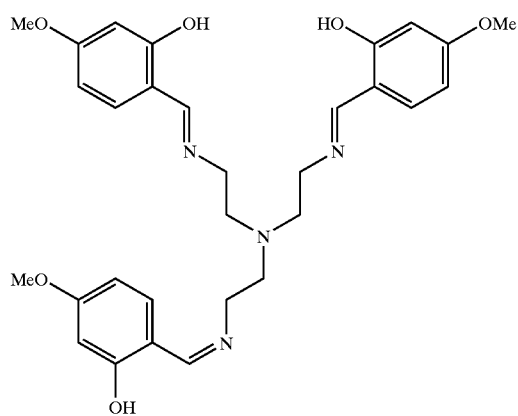

A suspension of 1.60 g (10.3 mmol) of 2-hydroxy-4methoxybenzaldehyde, 527 µl (3.42 mmol) of tris(2-aminoethyl)amine and 10 g of molecular sieve (3 Å) in 90 ml of absolute ethanol is prepared, reacted and worked up as described in Example 2.

Yield: 1.68 g (83%), reddish brown solid.

$^{13}$C NMR (CDCl$_3$): δ=55.7 (O$\underline{C}$H$_3$), 56.1, 56.3 (N—$\underline{C}$H$_2$), 101.7, 106.5, 133.8 (tert. aryl-C), 112.3, 164.4, 167.7 (quart. aryl-C); 165.4 (C=N).

EXAMPLE 5

N,N',N''-Tris[4-hydroxysalicylideneaminoethyl]amine

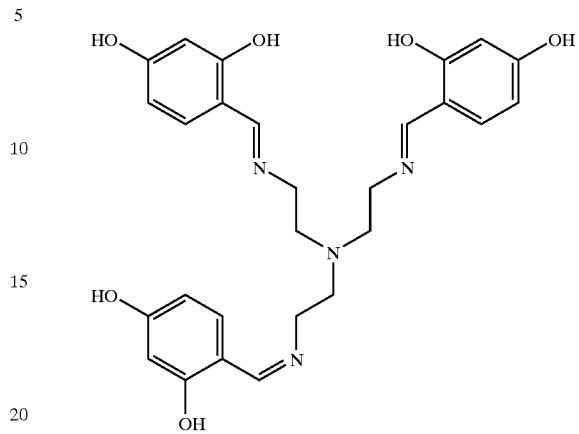

A suspension of 1.452 g (10.3 mmol) of 2,4-dihydroxybenzaldehyde in 90 ml of 96% ethanol is reacted with 527 µl (3.42 mmol) of tris(2-aminoethyl)amine as described in Example 2. The reaction solution is stirred at room temperature for 8 hours. To work up, the precipitate formed is filtered off and dried to constant weight at 40° C. under reduced pressure.

Yield: 1.54g (89%), yellowish orange solid.

$^{13}$C NMR (DMSO): δ=54.9, 55.0 (N—$\underline{C}$H$_2$), 102.7, 106.5, 133.5 (tert. aryl-C), 110.8, 162.1, 166.2 (quart. aryl-C), 164.9 (C=N).

EXAMPLE 6

N,N', N''-Tris[5-nitrosalicylideneaminoethyl]amine

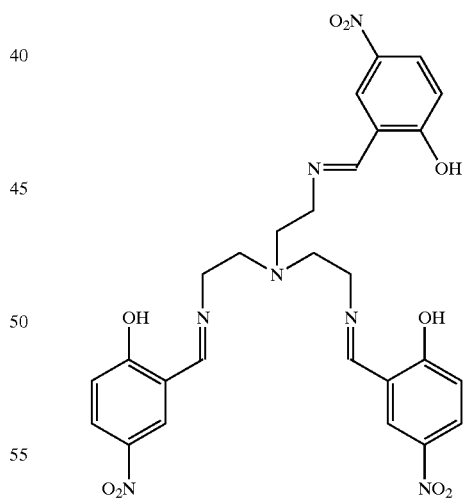

527 µl (3.42 mmol) of tris(2-aminoethyl)amine are added dropwise to a suspension of 1.775 g (10.3 mmol) of 2-hydroxy-5-nitrobenzaldehyde in 90 ml of absolute ethanol. After stirring at room temperature for eight hours, the product is filtered off and dried as described in Example 5.

Yield: 1.97 g (97%), yellowish orange solid.

$^{13}$C NMR (DMSO): δ=50.2, 52.9 (N—$\underline{C}$H$_2$), 122.3, 128.7, 133.5 (tert. aryl-C.) 167.1 (C=N), 113.3, 132.2, 177.3 (quart. aryl-C).

EXAMPLE 7

N,N',N''-Tris[(4-N-methyl-N-isopropylamino)salicylideneaminoethyl]amine

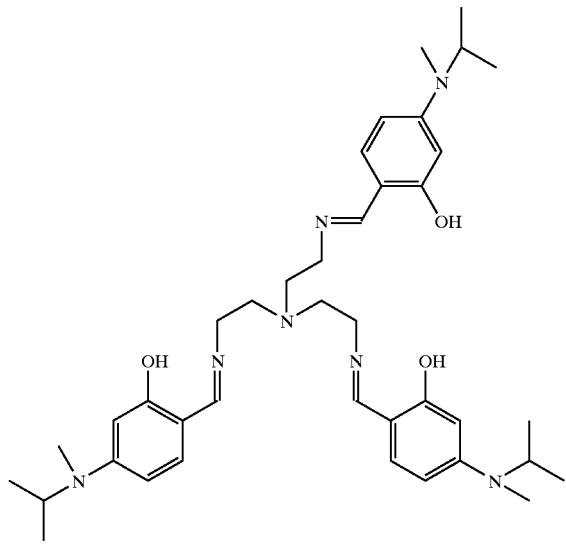

79.6 μl (0.52 mmol) of tris(2-aminoethyl)amine are added dropwise to a solution of 0.3 g (1.55 mmol) of 4-(N-isopropyl-N-methylamino)-2-hydroxybenzaldehyde in 14 ml of absolute ethanol at room temperature. The resulting reaction solution is stirred for 8 hours, concentrated, and dried to constant weight at 40° C. in a high vacuum.

Yield 352 mg (101 %), reddish brown solid, still contains ethanol.

$^{13}$C NMR (CDCl$_3$): δ=21.3 (NCH(CH$_3$)$_2$), 31.4 (NCH$_3$), 49.9 (NCH (CH$_3$)$_2$), 56.5, 57.9 (N—CH$_2$), 101.3, 105.0, 135.4 (tert. aryl-C), 110.3, 155.5, 169.9 (quart. C), 165.8 (C=N).

EXAMPLE 8

N,N',N''-Tris[(4-N-methyl-N-ethylamino)salicylideneaminoethyl]amine

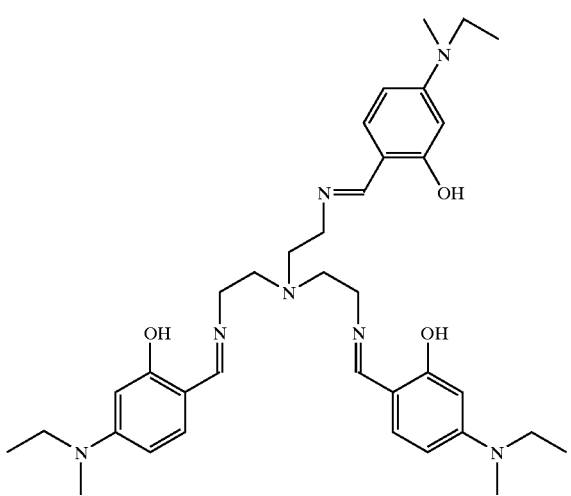

85.6 μl (0.56 mmol) of tris(2-aminoethyl)amine are added dropwise to a solution of 0.3 g (1.55 mmol) of 4-(N-ethyl-N-methylamino)-2-hydroxybenzaldehyde in 15 ml of absolute ethanol at room temperature. The resulting reaction solution is stirred for 2 hours at 50° C., and for a further 8 hours at room temperature. The workup is carried out as described in Example 7.

Yield 310 mg (89%), reddish brown resin.

$^{13}$C NMR (CDCl$_3$): δ=10.6 (NCH$_2$CH$_3$), 36.3 (NCH$_3$), 45.3 (NCH$_2$CH$_3$), 53.5, 55.0 (NCH$_2$), 98.0, 101.7, 132.7 (tert. aryl-C), 107.3, 151.8, 167.4 (quart. aryl-C); 162.9 (C=N).

EXAMPLE 9

N,N',N''-Tris[4-methylsalicylideneaminoethyl]amine

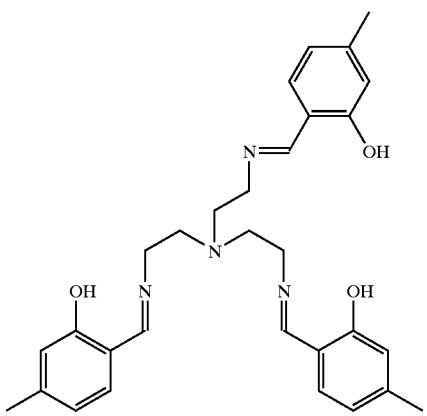

Example 7 is repeated starting with a reaction solution of 0.3 g (2.20 mmol) of 2-hydroxy-4-methylbenzaldehyde and 112.8 μl (0.73 mmol) of tris(2-aminoethyl)amine in 20 ml of absolute ethanol at room temperature.

Yield: 383 mg (105%), yellow solid, still contains ethanol.

$^{13}$C NMR (CDCl$_3$): δ=22.2 (CH$_3$), 56.3, 58.2 (NCH$_2$), 117.6, 119.9, 132.1 (tert. aryl-C), 116.7, 143.2, 161.8 (quart. aryl-C), 166.2 (C=N).

EXAMPLE 10

N,N', N''-Tris[4-trimethylammoniosalicylideneaminoethyl]amine tribromide

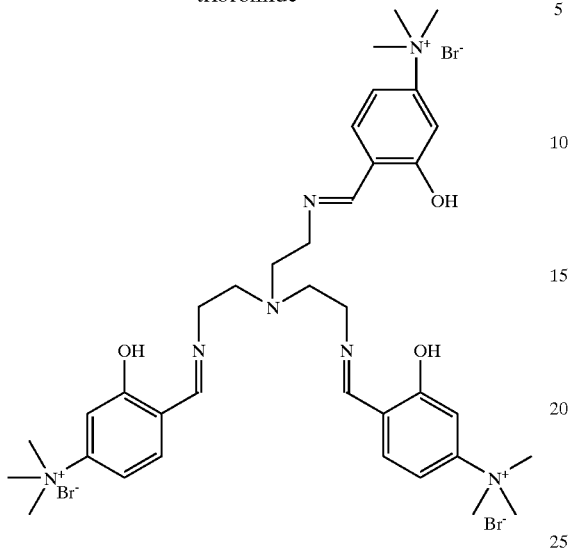

Example 7 is repeated starting with a reaction solution of 0.3 g (1.15 mmol) of 4-formyl-3-hydroxyphenyltrimethylammonium bromide (synthesis method: M. Ando, S. Emoto, Bull. Chem. Soc. Jpn., 42 (9) 2624 (1969)) in 10 ml of absolute ethanol and 59.0 µl (0.38 mmol) of tris(2-aminoethyl)amine.

Yield: 307 mg (93%), yellow solid.

$^{13}$C NMR (DMSO): δ=54.3, 54.8 (N$\underline{C}H_2$), 56.0 (—N$^+$—($\underline{C}H_3)_3$), 108.3, 110.3, 133.3 (tert.aryl-C), 118.1, 125.3, 150.3 (quart. aryl-C), 165.0 (C=N).

EXAMPLE 11

N,N',N''-Tris[5-trimethylammoniosalicylideneaminoethyl]amine tribromide

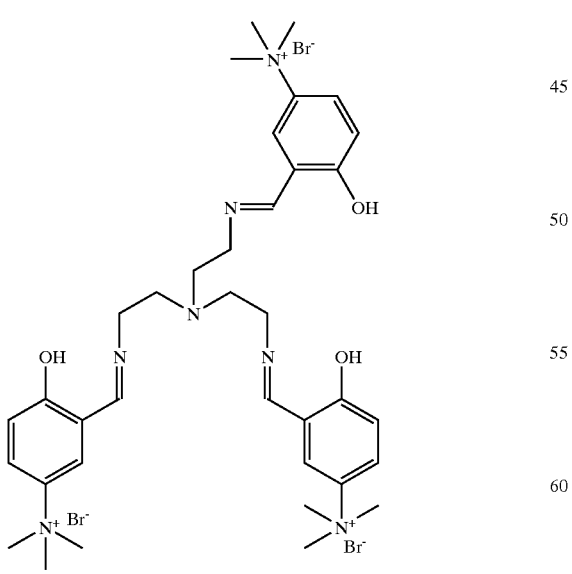

Example 7 is repeated starting with a reaction solution of 0.3 g (1.15 mmol) of 3formyl4-hydroxyphenyltrimethylammonium bromide [synthesis method: M. Ando, S. Emoto, Bull. Chem. Soc. Jpn., 42 (9) 2624 (1969)] in 10 ml of absolute ethanol and 59.0 µl (0.38 mmol) of tris(2-aminoethyl)amine.

Yield: 320 mg (97%), orange solid.

$^{13}$C NMR (DMSO-d$_6$): δ=54.3, 55.4 (N$\underline{C}H_2$), 56.4 (N$^+$($\underline{C}H_3$)$_3$), 119.0, 123.1, 124.6 (tert. aryl-C), 117.4, 136.5, 164.0, 164.8 (quart. aryl-C), 164.5 (C=N).

EXAMPLE 12

N,N',N''-Tris[5-sulfonatosalicylideneaminoethyl]amine, trisodium salt

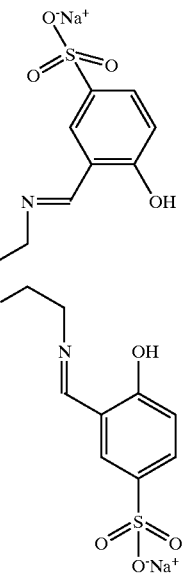

226 µl (221.2 mg, 1.482 mmol) of tris(2-aminoethyl)amine are added dropwise to a suspension of 1 g (4.46 mmol) of sodium salicylaldehyde-5-sulfonate in 120 ml of ethanol. After stirring at room temperature for 24 hours, the crude product is filtered off and washed with a little cold ethanol. The crude product is dried in a high vacuum at 35° C.

Yield: 870 mg (77%), lemon yellow solid.

$^{13}$C NMR (DMSO-d$_6$): δ=56.3, 57.7 (N—$\underline{C}H_2$), 117.8, 130.6, 131.7 (tert. aryl-C), 118.4, 139.5, 163.9 (quart. aryl-C), 167.9 (C=N),

EXAMPLE 13

Synthesis of the unsubstituted manganese(III) complex

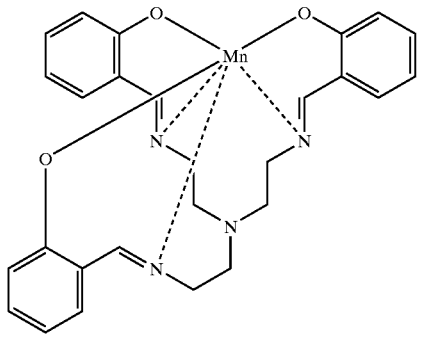

The 1:1 manganese complex is synthesized by reacting 1.50 g (5.6 mmol) of manganese(III) acetate dihydrate with 2.43 g (5.3 mmol) of N,N',N''-tris[salicylideneaminoethyl]amine from Example 1 by the literature method of A. Chakravorty et al. [S. K Chandra, P. Chakraborty and A. Chakravorty, *J. Chem. Soc., Dalton Trans.* (1993) 863].

Yield: 2.40 g (89%), greenish olive powder.

Elemental analysis $C_{27}H_{27}MnN_4O_3*CH_3OH$ (542.52)

| rec. | 62.00 | H 5.76 Mn 10.13 | N 10.33 |
| --- | --- | --- | --- |
| obs. | 62.85 | H 5.54 Mn 10.4 | N 10.63 |

Alternatively, the manganese(III) complex is synthesized by the literature method of R. Mukherjee et al. [K. Ramesh, D. Bhuniya and R. N. Mukherjee, *J. Chem. Soc., Dalton Trans.* (1991) 2917] by reacting 8.00 g (17.4 mmol) of N,N',N''-tris[salicylideneaminoethyl]-amine with 6.41 g (26.2 mmol) of manganese(II) acetate tetrahydrate and subsequent oxidation.

Yield: 728 g (76%).

The manganese(III) complexes prepared perform well in DTI screening (see application examples, Table 1).

Application Examples

EXAMPLE 14

The catalysts were tested for DTI activity. The DTI (dye transfer inhibition) effect a is defined as the following percentage:

$$a=([Y(E)-Y(A)]/[Y(W)-Y(A)])*100$$

where Y(W), Y(A) and Y(E) are the CIE lightnesses of the white material, of the material treated without added catalyst and of the material treated with added catalyst, in that order. a=0 characterizes a product of nil utility, the inclusion of which in the wash liquor does nothing to impede dye transfer. a=100%, by contrast, defines a perfect catalyst, which completely suppresses the tainting of the white material.

The test data are determined using the following testing system: 7.5 g of white cotton are treated in 80 ml of wash liquor. This liquor contains the standard detergent ECE phosphate-free (456 IEC) EMPA, Switzerland, in a concentration of 7.5g/l, 8.6 mmol/l $H_2O_2$, and a solution of the test dye. The washing process is carried out in a pot in a LINITEST apparatus at 40° C. for 30 min. Commercially available Direct Brown 172 (dye 1) at 10 mg/l of the 250% formulation or Reactive Blue 238 (dye 2) at 6 mg/l of the 100% formulation were used as test dyes. The reflectants spectra of the samples were measured with a SPECTRAFLASH 2000 and transformed into D65/10 lightnesses by the CIE standard procedure.

Table 1 shows the DTI effects a(%) of 1:1 manganese complexes of the ligands of Examples 1–12 and of the manganese complex of Example 13.

The manganese complexes are synthesized either as described in Example 13 or in situ by adding the corresponding manganese(III) salt in ethanolic solution. The complexes are always used at 20 μmol/l wash liquor. It is evident from the table that the recited catalysts are very effective DTI catalysts.

TABLE 1

| | DTI effect a(%) | |
| --- | --- | --- |
| Manganese complex of ligand of example | Dye 1 | Dye 2 |
| 1 (by in situ method) | 91 | 96 |
| 2 | 78 | 73 |
| 3 | 85 | 80 |
| 4 | 83 | 67 |
| 5 | 78 | 27 |
| 6 | 70 | 80 |
| 7 | 84 | 83 |
| 8 | 85 | 81 |
| 9 | 87 | 94 |
| 10 | 90 | 96 |
| 11 | 86 | 94 |
| 12 | 80 | 99 |
| 13 (isolated manganese complex of ligand of Example 1) | 99 | 95 |

EXAMPLE 15

Table 2 shows that the manganese complex of the ligand of Example 1 is very effective in inhibiting the redeposition of dyes of various classes. The experimental conditions are described in Example 14. The use concentration of the catalyst is 10 μmo/l.

TABLE 2

| Test dye | Dye concentration mg/l | DTI effect [a (%)] |
| --- | --- | --- |
| Direct Brown 172 250% | 10 | 79 |
| Reactive Blue 238 100% | 6 | 98 |
| Reactive Black 005 133% | 12 | 54 |
| Reactive Black 022 400% | 6 | 73 |
| Reactive Blue 019 special 100% | 20 | 85 |
| Acid Blue 113 180% | 6 | 98 |
| Disperse Violet 001 100% | 6 | 79 |

EXAMPLE 16

The ligands of the invention enhance the bleaching effect of hydrogen peroxide in wash liquors significantly. The bleach tests are carried out as follows: 7.5 g of white cotton fabric and 2.5 g of a tea stain on cotton fabric are treated in 80 ml of wash liquor. This liquor contains the standard laundry detergent ECE phosphate-free (456 IEC) EMPA, Switzerland in a concentration of 7.5 g/l, hydrogen peroxides in a concentration of 8.6 mmol/l and optionally 100 μmol/l of one of the ligands according to the invention. The washing process takes place in a steel pot in a LINITEST apparatus at 40° C. for 30 minutes. The bleaching results are evaluated using the increase in lightness DY (lightness difference as per CIE) of the stain due to the treatment. Table 3 contains the DY values for the systems tested.

TABLE 3

| DY with $H_2O_2$ only | DY with $H_2O_2$ and ligand of Example 2 | DY with $H_2O_2$ and ligand of Example 3 | DY with $H_2O_2$ and ligand of Example 7 | DY with $H_2O_2$ and ligand of Example B |
|---|---|---|---|---|
| 18 | 21 | 22 | 21 | 22 |

EXAMPLE 17

The manganese complex of the ligand of Example 1 is associated with a level of damage on coloured laundry that is acceptable. With regard to dye damage, less degradation is observed than with the TAED-activated bleaching system, even with regard to dyes known to be very sensitive. The TAED-activated bleaching system is considered to be the best oxygen bleaching technology has to offer, and its damage/benefit ratio is accepted. Use as described above gives the following percentage dye loss after fivefold treatment.

TABLE 4

| | Dye loss % | |
|---|---|---|
| Test dyeing | Catalyst 50 μmol/l | TAED |
| Vat Brown 001 | 5 | 5 |
| Reactive Brown 017 | 5 | 15 |
| Reactive Red 123 | 5 | 10 |
| Direct Blue 085 | 15 | 15 |
| Vat Blue 004 | 0 | 5 |
| Reactive Black 005 | 15 | 25 |

EXAMPLE 18

The manganese complex of the ligand of Example 1 is similar with regard to fibre damage on dyed materials to the cited TAED system. Use as described above gives the following relative DP reduction after fivefold treatment.

TABLE 5

| | relative DP reduction % | |
|---|---|---|
| Test dyeing | Catalyst 50 μmol/l | TAED |
| Reactive Brown 017 | 15 | 15 |
| Vat Brown 001 | 5 | 5 |
| Reactive Red 123 | 5 | 0 |
| Direct Blue 085 | 10 | 5 |
| Vat Blue 004 | 5 | 0 |
| Reactive Black 005 | 5 | 5 |

EXAMPLE 19

Providing a Liquid Preparation 20 g of the catalyst of Example 13, 4 g of a nonionic dispersant (block polymers of ethylene oxide and propylene oxide, tradename: Pluronic F108), 176 g of deionized water and 400 g of glass beads (Ø0.5 mm) are stirred at 850 rpm in a grinding pot at 20° C. for 3 hours. The glass beads are then filtered off. A liquid preparation of the catalyst is obtained.

EXAMPLE 20

Providing a Solid Preparation 0.1 g of the catalyst of Example 13 and 0.9 g of anhydrous sodium sulfate were thoroughly triturated using a mortar and pestle.

EXAMPLE 21

Use Example for Solid and Liquid Preparations

The liquid and solid preparations of Examples 19 and 20 were tested for their DTI effect a(%) (see Exampl 14). Th test data are determined using the testing system of Example 14, except that this time 0.25 g of a piece of cotton dyed with the dye Direct Black 22 (EMPA, Switzerland) is used as dye donor. The catalyst concentration in the wash liquor is always 50 μmol. In the experiments, the catalyst is added to the testing system in five different forms: i) as a solid without further treatment, ii) in the form of a concentrated solution in DMF, iii) in the form of the suspension of Example 19, iv) in the form of the solid preparation of Example 20, v) 1.7 g of the suspension of Example 19 is thoroughly mixed with 48.3 g of laundry detergent (IEC 456 Type A) and 40 g of water in a grinding dish and dried at room temperature under reduced pressure for 50 hours. The laundry detergent thus formed is then classified, and the 315–800 μm fraction is used for the washing test. This test is carried out with 7.5 g/l of this laundry detergent instead of 7.5 g/l of the standard laundry detergent (IEC 456 Type A).

Table 6 shows the DTI effects a(%). The table shows that the solid preparation, the suspension and the suspension incorporated into the laundry detergent all provide superior DTI effects than the untreated, solid catalyst and than the dissolved catalyst.

TABLE

| Catalyst system | DTI effect a(%) |
|---|---|
| i) Catalyst is solid | 49 |
| ii) Catalyst dissolved in DMF | 0 |
| iii) Catalyst triturated with $Na_2SO_4$ | 75 |
| iv) Catalyst suspension | 71 |
| v) Catalyst suspension incorporated into laundry detergent | 83 |

What is claimed is:

1. A process for oxidation, which comprises oxidizing an oxidizable substrate with a mixture of a peroxygen compound and, as oxidation catalyst, a Mn(III) or Fe(III) metal complex containing a tripodal ligand of the formula

23

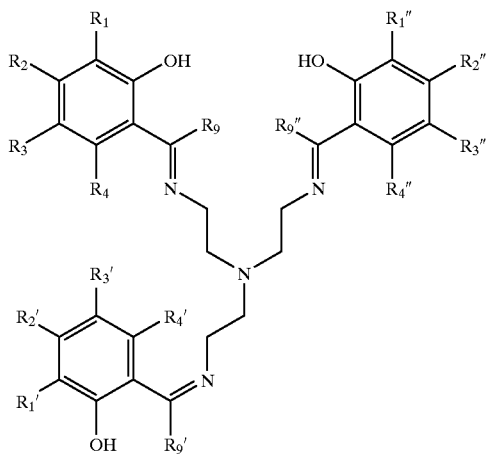

(1)

where $R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano halogen, $SO_3M$, where M is hydrogen, an alkali metal cation, an alkaline earth metal cation, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $NR_6R_7$, $N\oplus R_6R_7R_{10}$ or linear or branched $C_1$–$C_8$alkyl-$R_8$, where $R_8$ is $OR_5$, $COOR_5$, $NH_2$, $NHR_6$, $NR_6R_7$ or $N\oplus R_6R_7R_{10}$, where $R_6$, $R_7$ and $R_{10}$ are indentical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl.

2. A process according to claim 1, in which the metal complex is a 1:1 metal(III) complex of the formula

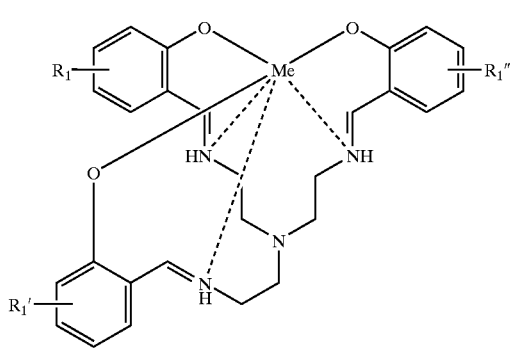

(2)

where Me is Mn or Fe, $R_1$, $R_1'$ and $R_1''$ are each independently hydrogen, $C_1$–$C_4$alkyl, $C_1$–$C_4$alkoxy, hydroxyl, nitro, $NHR_6$, $NR_6R_7$ or —$N\oplus R_5R_6R_7$, where $R_5$, $R_6$ and $R_7$ are each independently $C_1$–$C_4$alkyl.

3. A process according to claim 2, wherein the metal complex is an Mn(III) complex.

4. A process according to claim 1, wherein a tripodal ligand of the formula (1) is used in an aqueous solution together with a peroxygen compound for bleaching spots or stains on textile material.

5. A process according to claim 1, wherein the tripodal ligand conforms to the formula

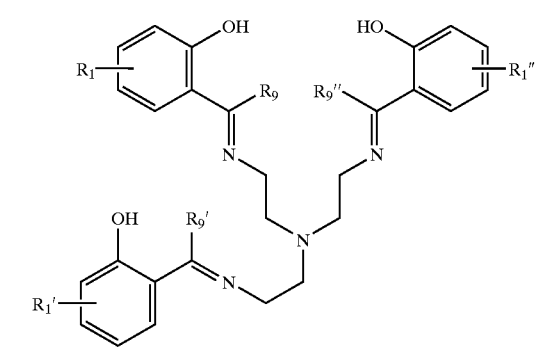

(3)

where $R_1$, $R_1'$ and $R_1''$ are each independently hydrogen, $C_1$–$C_4$alkyl, $C_1$–$C_4$alkoxy, hydroxyl, nitro, $NHR_6$, $NR_6R_7$ or $N\oplus R_5R_6R_7$, where $R_5$, $R_6$ and $R_7$ are each independently $C_1$–$C_4$alkyl and $R_9$, $R_9'$ and $R_9''$ are each independently hydrogen, linear or branched $C_1$–$C_8$alkyl or aryl.

6. A manganese(III) or iron(III) complex containing a tripodal ligand of the formula

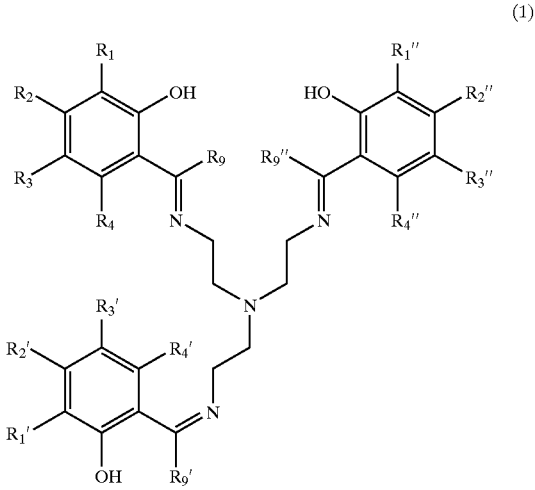

(1)

where $R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano, —Cl, F, $SO_3M$, where M is hydrogen, an alkali metal cation, an alkaline earth metal cation, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $NR_6R_7$, $N\oplus R_6R_7R_{10}$ or linear or branched $C_1$–$C_8$alkyl-$R_8$, where $R_8$ is $OR_5$, $COOR_5$, $NH_2$, $NHR_6$, $NR6R_7$ or $N\oplus R_6R_7R_{10}$, where $R_6$, $R_7$ and $R_{10}$ are identical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl, subject to the condition that in the manganese(III) complex at least one of the substituents $R_1$, $R_2$, $R_3$, $R_4$, $R_1'$, $R_2'$, $R_3'$, $R_4'$, $R_1''$, $R_2''$, $R_3''$, $R_4''$, $R_9$, $R_9'$ and $R_9''$ has a meaning other than hydrogen and that at least one of the substituents $R_3$, $R_3'$ and $R_3''$ has a meaning other than chlorine when the substituents $R_1$, $R_2$, $R_4$, $R_1'$, $R_2'$, $R_4'$, $R1''$, $R2''$, $R4''$, $R9$, $R9'$ and $R9''$ are all hydrogen.

7. A ligand of the formula

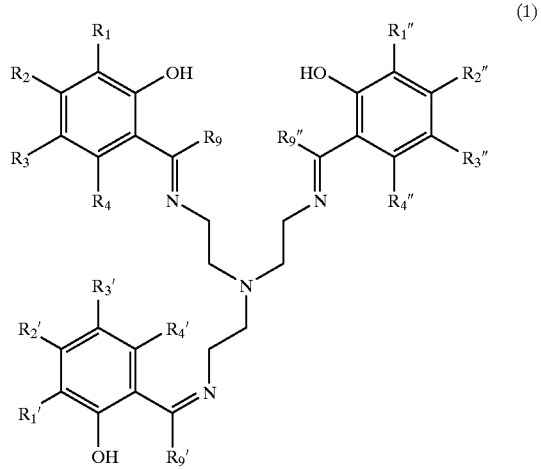

(1)

where $R_1$, $R_2$, $R_3$, $R_4$, $R_1'$, $R_2'$, $R_3'$, $R_4'$, $R_1''$, $R_2''$, $R_3''$ and $R_4''$ are each independently hydrogen, cyano, —Cl, F, $SO_3M$, where M is hydrogen, an alkali metal cation, an alkaline earth metal cation, ammonium or an organic ammonium cation, $SO_2NH_2$, $SO_2NHR_5$, $SO_2N(R_5)_2$, $OR_5$ or $COOR_5$, where $R_5$ is hydrogen or linear or branched $C_1$–$C_4$alkyl, nitro, linear or branched $C_1$–$C_8$alkyl, linear or branched fluorinated or perfluorinated $C_1$–$C_8$alkyl, $NHR_6$, $NR_6R_7$, $N{\oplus}R_6R_7R_{10}$ or linear or branched $C_1$–$C_8$alkyl-$R_8$, where $R_8$ is $OR_5$, $COOR_5$, $NH_2$, $NHR_6$, $NR_6R_7$ or $N{\oplus}R_6R_7R_{10}$, where $R_6$, $R_7$ and $R_{10}$ are identical or different and each is linear or branched $C_1$–$C_{12}$alkyl or where $R_6$ and $R_7$ combine with the joining nitrogen atom to form a 5-, 6- or 7-membered ring, which may contain further heteroatoms, and where $R_9$, $R_9'$ and $R_9''$ are each independently hydrogen, linear or branched $C_1$–$C_8$alkyl or aryl, subject to the condition that in the manganese(III) complex at least one of the substituents $R_1$, $R_2$, $R_3$, $R_4$, $R_1'$, $R_2'$, $R_3'$, $R_4'$, $R_1''$, $R_2''$, $R_3''$, $R_4''$, $R_9$, $R_9'$ and $R_9''$ has a meaning other than hydrogen and that at least one of the substituents $R_3$, $R_3'$ and $R_3''$ has a meaning other than chlorine when the substituents $R_1$, $R_2$, $R_4$, $R_1'$, $R_2'$, $R_4'$, $R_1''$, $R_2''$, $R_4''$, $R_9$, $R_9'$ and $R_9''$ are all hydrogen.

8. A washing or cleaning process, which comprises adding to a liquor which contains a peroxidic detergent, 0.1 to 200 μmol per liter of wash liquor of one or more metal complexes or an uncomplexed ligand of the formula (1) according to claim 7.

9. A process for preventing the redeposition of migrating dyes in a wash liquor, which comprises adding to the wash liquor, which contains a peroxidic detergent, 0.5 to 150 mg per liter of wash liquor of one or more metal complexes containing a tripodal ligand of the formula (1) as defined in claim 1.

10. A laundry detergent comprising

I) 5–90% of A) an anionic surfactant and/or B) a nonionic surfactant,

II) 5–70% of C) a builder,

III) 0.1–30% of D) a peroxide, and

IV) 0.005–2% of E) a metal complex containing a tripodal ligand of the formula (1) as defined in claim 22, the percentages all being percent by weight based on the total weight of the laundry detergent.

11. A process according to claim 1, in which a hard surface is cleaned.

12. A hard surface cleaner, which comprises a peroxygen compound and a metal complex containing a tripodal ligand of the formula (1) as defined in claim 1 as catalyst for the peroxygen compound.

13. A hard surface cleaner according to claim 12, which is an automatic dishwasher cleaning composition.

14. A process for cleaning crockery, which comprises using a hard surface cleaner according to claim 13.

15. A process according to claim 11, wherein the hard surfaces which are cleaned are tiles and inter-tile joints.

16. A process according to claim 1, which is a process for killing bacteria or for protecting a surface against bacterial colonization.

17. An aqueous suspension comprising a) 1–60% by weight of a metal complex containing a tripodal ligand of the formula (1) as defined in claim 1, b) 0.5 to 15% by weight of a dispersant, c) 0–10% by weight of a further ingredient, and d) 15–98.5% by weight of water.

18. A solid preparation comprising a) 1–99% by weight of a metal complex containing a tripodal ligand of the formula (1) as defined in claim 1, b) 1 to 99% by weight of a carrier material, c) 0–20% by weight of a dispersant, d) 0–10% by weight of a further ingredient, and e) 0–5% by weight of water.

19. An aqueous suspension according to claim 17, wherein the metal complex containing a tripodal ligand of the formula (1) as defined therein has an average particle size of less than 20 μm.

20. A solid preparation according to claim 18, wherein the metal complex containing a tripodal ligand of the formula (1) as defined therein has an average particle size of less than 20 μm.

21. A process according to claim 1, which is a process for removing printing inks from printed waste paper (de-inking).

* * * * *